United States Patent [19]

Sturm et al.

[11] Patent Number: 4,847,258

[45] Date of Patent: Jul. 11, 1989

[54] SUBSTITUTED BENZOYLPHENYLUREAS COMPOUNDS USEFUL AS PESTICIDES

[75] Inventors: Elmar Sturm, Aesch; Robert W. Lang, Pratteln; Odd Kristiansen, Möhlin, all of Switzerland

[73] Assignee: Ciba-Geigy Corporation, Ardsley, N.Y.

[21] Appl. No.: 86,339

[22] Filed: Aug. 17, 1987

[30] Foreign Application Priority Data

Aug. 26, 1986 [CH] Switzerland ............... 3422/86-0
Jul. 23, 1987 [CH] Switzerland ............... 2795/87-8

[51] Int. Cl.$^4$ ............... A01N 43/54; C07D 239/34
[52] U.S. Cl. ............... 514/274; 544/316
[58] Field of Search ............... 544/316; 514/274

[56] References Cited

U.S. PATENT DOCUMENTS 4,552,900 11/1985 Sirrenberg et al. ............... 544/319
4,627,871 12/1986 Sasse et al. ............... 544/316

FOREIGN PATENT DOCUMENTS 3311703 10/1984 Fed. Rep. of Germany ...... 544/316
2122494 1/1984 United Kingdom ............... 514/274
2171695 9/1986 United Kingdom ............... 544/316

OTHER PUBLICATIONS

Derwent Abstract of Japanese J56015272 (2/81) Ishihara Sargyo Kaisha, Ltd.

Primary Examiner—Richard A. Schwartz
Assistant Examiner—Zinna Northington
Attorney, Agent, or Firm—Kevin T. Mansfield; Edward McC. Roberts

[57] ABSTRACT

The invention relates to novel N-benzoyl-N,-4-(5-phenylpyrimid-2-yloxy)phenylureas of formula

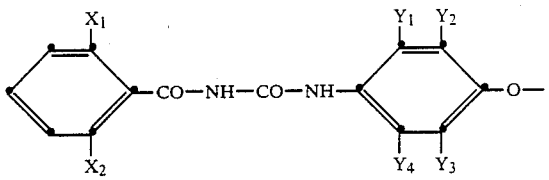

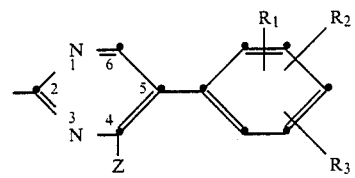

wherein
  $X_1$ is hydrogen, halogen, $C_1$–$C_3$alkoxy or $C_1$–$C_3$alkylthio,
  $X_2$ is halogen, methyl, $C_1$–$C_3$alkoxy or $C_1$–$C_3$alkylthio,
  $Y_1$, $Y_2$, $Y_3$ and $Y_4$ are each independently hydrogen, halogen, methyl, trifluoromethyl or methoxy,
  Z is methyl, halomethyl containing 1 to 3 halogen atoms or pentafluoroethyl; and
  $R_1$, $R_2$ and $R_3$ are each independently hydrogen, halogen, $C_1$–$C_3$alkyl, trifluoromethyl or $C_1$–$C_3$alkoxy, to the preparation thereof and to intermediates for the synthesis of these compounds, as well as to compositions containing them for use in pest control, especially for controlling representatives of the order Acarina that attack plants and animals and for controlling insects. The novel compounds exhibit especially pronounced activity against plant-destructive mites.

20 Claims, No Drawings

SUBSTITUTED BENZOYLPHENYLUREAS COMPOUNDS USEFUL AS PESTICIDES

The present invention relates to novel substituted N-benzoyl-N'-4-(5-phenylpyrimidin-2-yloxy)-phenylureas, to the preparation thereof and to intermediates for the synthesis of these compounds, and to the use of the novel compounds in pest control.

The compounds of this invention have the formula I

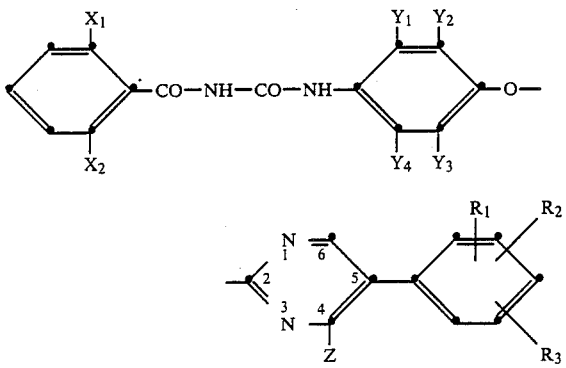

wherein
$X_1$ is hydrogen, halogen, $C_1$-$C_3$alkoxy or $C_1$-$C_3$alkylthio,
$X_2$ is halogen, methyl, $C_1$-$C_3$alkoxy or $C_1$-$C_3$alkylthio,
$Y_1$, $Y_2$, $Y_3$ and $Y_4$ are each independently hydrogen, halogen, methyl, trifluoromethyl or methoxy,
Z is methyl, halomethyl containing 1 to 3 halogen atoms or pentafluoroethyl; and
$R_1$, $R_2$ and $R_3$ are each independently hydrogen, halogen, $C_1$-$C_3$alkyl, trifluoromethyl or $C_1$-$C_3$alkoxy.

Preferred compounds of formula I are those wherein
$X_1$ is hydrogen, halogen, $C_1$-$C_3$alkoxy or $C_1$-$C_3$alkylthio,
$X_2$ is halogen, methyl, $C_1$-$C_3$alkoxy or $C_1$-$C_3$alkylthio,
$Y_1$, $Y_2$, $Y_3$ and $Y_4$ are each independently hydrogen, halogen, methyl, trifluoromethyl or methoxy,
Z is methyl or halomethyl containing 1 to 3 halogen atoms; and
$R_1$, $R_2$ and $R_3$ are each independently hydrogen, halogen, $C_1$-$C_3$alkyl, trifluoromethyl or $C_1$-$C_3$alkoxy.

Preferred compounds of formula I on account of their pesticidal activity are those wherein
$X_1$ is hydrogen, halogen or methoxy,
$X_2$ is halogen or methoxy,
$Y_1$ and $Y_4$ are hydrogen,
$Y_2$ and $Y_3$ are each independently of the other hydrogen, fluorine, chlorine, methyl or trifluoromethyl,
Z is methyl, dichloromethyl, trichloromethyl, monofluoromethyl, difluoromethyl, trifluoromethyl, difluorochloromethyl or pentafluoroethyl; and
$R_1$, $R_2$ and $R_3$ are each independently hydrogen, fluorine, chlorine, bromine, methyl, ethyl, isopropyl, trifluoromethyl, methoxy or ethoxy.

Further preferred compounds of formula I are those wherein
$X_1$ is fluorine, chlorine or methoxy, and
$X_2$ is fluorine or chlorine, and those wherein
$Y_1$ and $Y_4$ are hydrogen, and
$Y_2$ and $Y_3$ are hydrogen, fluorine or chlorine.

Of particular biological interest are those compounds of formula I, wherein Z is trifluoromethyl, difluorochloromethyl or pentafluoroethyl; those wherein $R_1$ is hydrogen, $R_2$ is hydrogen, 2-fluoro or 2-chloro, and $R_3$ is hydrogen, 4-fluoro or 4-chloro; and also those wherein $X_1$ and $X_2$ are fluorine and $R_1$, $R_2$ and $R_3$ are hydrogen; as well as those wherein $Y_1$ is methyl.

Exemplary of alkyl groups in $C_1$-$C_3$alkyl, $C_1$-$C_3$alkoxy or $C_1$-$C_3$alkylthio in the above definitions are methyl, ethy, n-propyl, and isopropyl. Within the scope of this invention, halogen will be understood as meaning fluorine, chlorine, bromine and iodine, with fluorine and chlorine being preferred.

The compounds of formula I can be obtained by processes analogous to known ones (q.v. inter alia German Offenlegungsschrift specifications Nos. 2 123 236, 2 601 780 and 3 240 975).

Thus, for example, a compound of formula I can be obtained by (a) reacting a compound of formula II

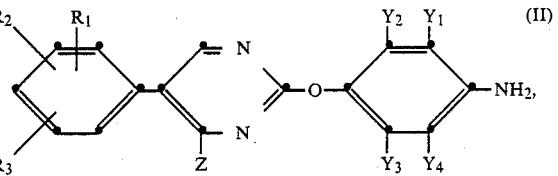

with a compound of formula III

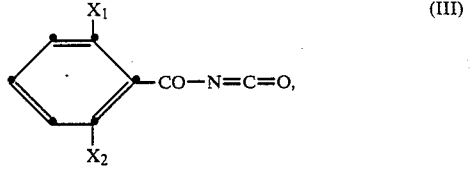

or (b) reacting a compound of formula IV

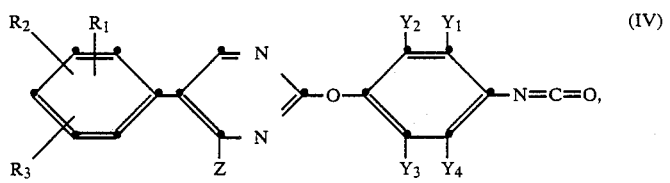

with a compound of formula V

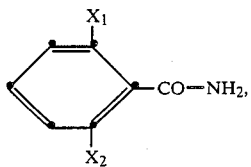

or (c) reacting a compound of formula II with a compound of formula VI

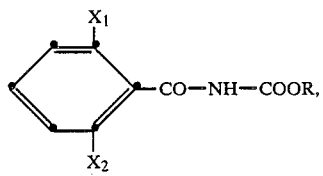

in which formulae II to VI the substituents $X_1$, $X_2$, $Y_1$ to $Y_4$, Z and $R_1$ to $R_3$ have the meanings given above and R is a $C_1$–$C_3$alkyl radical which is unsubstituted or substituted by halogen, preferably chlorine.

The above processes (a), (b) and (c) are preferably carried out under normal pressure and in the presence of an organic solvent or diluent. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; dimethyl sulfoxide; and ketones, e.g. acetone, methyl ethyl ketone, methyl isopropyl ketone and methyl isobutyl ketone. Process (a) is normally carried out in the temperature range from $-10°$ to 200° C., preferably from 30° to 150° C., and, if desired, in the presence of an organic base such as triethylamine. Process (b) is carried out in the temperature range from 0° to 150° C., preferably at the boiling point of the solvent employed and, if desired, in the presence of an organic base such as pyridine, and/or with the addition of an alkali metal or alkaline earth metal, preferably sodium. For process (c), i.e. for the reaction of the urethane of formula VI with a pyridyloxyaniline of formula II, a temperature range from about 60° C. to the boiling of the reaction mixture is preferred, and the solvent employed is preferably an aromatic hydrocarbon such as toluene, a xylene, chlorobenzene and the like.

The starting materials of formulae III, V and VI are known or they can be prepared by methods analogous to known ones. The starting materials of formula II and IV are novel compounds which likewise constitute an object of the present invention. The 5-phenylpyrimid-2-yloxyanilines of formula II can be prepared by reacting a 5-phenylpyrimidine of formuly VII

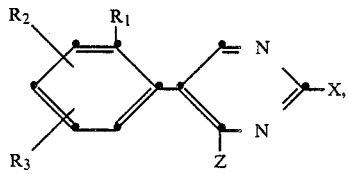

which can be reacted in 2-position, with a p-aminophenol of formula VIII

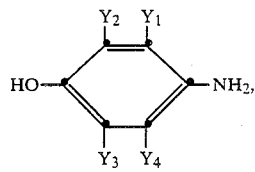

in which formulae VII and VIII the substituents $Y_1$ to $Y_4$, Z and $R_1$ to $R_3$ are as defined above and X is halogen, preferably chlorine, or $-SO_2CH_3$.

The substituted 5-phenylpyrimidines of formula VII can be obtained in per se known manner as follows [q.v. Arch. Pharmaz. Ber. dtsch. pharmaz. Ges. 317, 425 (1984)]:

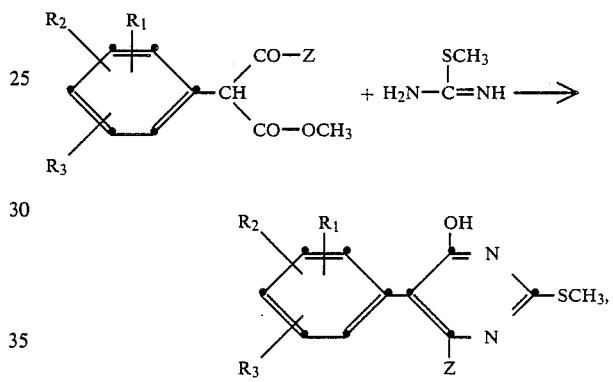

in which formulae above $R_1$ to $R_3$ and Z are as previously defined. The 4-hydroxy group is removed from the resultant 2-methylthio-4-hydroxy-5-phenylpyrimidine by halogenation with phosphoroxy chloride ($POCl_3$) and subsequent catalytic hydrogenation [q.v. Rec. 92, 1025 (1973); German patent specification 3 423 622]. The 2-methylthio-5-phenylpyrimidine so obtained of formula (X)

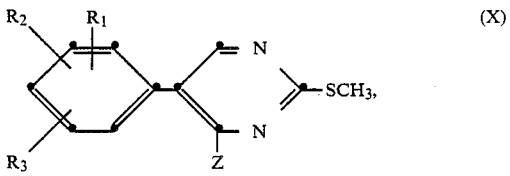

can be converted by oxidation, e.g. with p-chloroperbenzoic acid [q.v. J. Chem. Soc. C 568 1967)] into a compound of formula VII, wherein X is methylsulfonyl.

To prepare compounds of formula X and VII, wherein Z is trihalomethyl, preferably $-CF_3$ or $-CF_2Cl$, or pentaflauoroethyl, a novel process is proposed herein, which comprises reacting e.g. trifluoromethylcarbonylmethoxystyrene of formula IX with S-methylisothiourea:

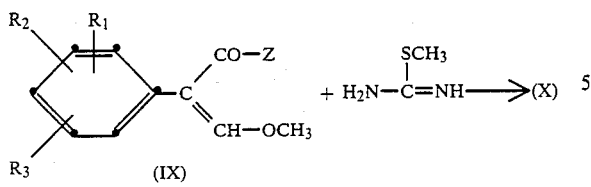

The resultant compound of formula X is then, as indicated above, converted into a corresponding 2-methylsulfonyl compound of formula VII

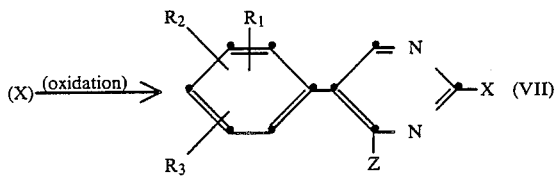

X = —SO$_2$CH$_3$
Z = trihalomethyl, —CF$_2$CF$_3$

A trihalomethylcarbonylmethoxystyrene or pentafluoroethylcarbonylmethoxystyrene of the above formula IX can be prepared by acylating the corresponding methoxystyrene, which is preferably halogen-substituted at the benzene ring, with an appropriate halogenated acid anhydride:

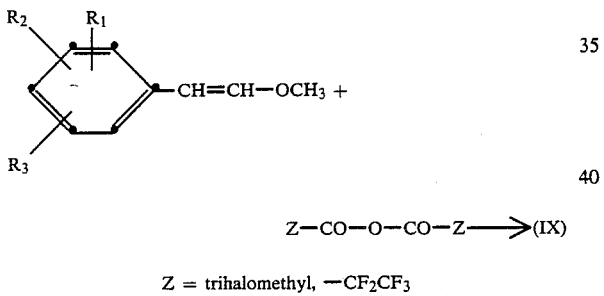

Z = trihalomethyl, —CF$_2$CF$_3$

This reaction can be carried out in a solvent, e.g. pyridine, or without a solvent, in a bomb tube (4 to 10 hours in the temperature range from about 80° to 120° C.).

Compounds of formula VII, wherein X is halogen, preferably chlorine, can be obtained by reacting a suitable methoxystyrene derivative of formula IX, in the presence of a base, with guanidine, preferably in salt form, e.g. with guanidine hydrochloride, and diazotising the resultant 2-aminopyridine of formula XI in conventional manner and converting it into a 2-halopyrimidine of formula VII:

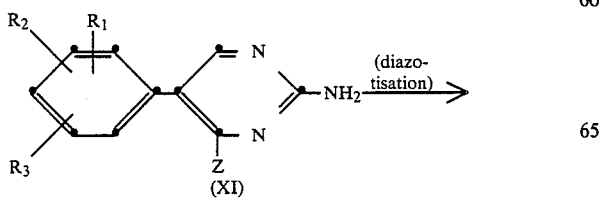

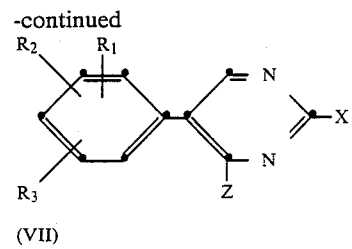

X = halogen
Z = trihalomethyl, —C$_2$F$_5$

A 5-phenylpyrimidine of formula VII, wherein X is halogen, preferably chlorine, and Z is methyl, can be obtained by halogenating, e.g. with POCl$_3$, a 2-hydroxy-4-methyl-5-phenylpyrimidine of the formula given below obtainable by the process described in German patent specification 3 315 797:

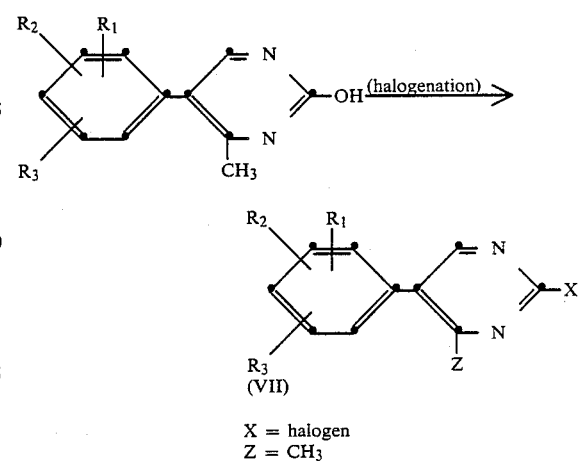

X = halogen
Z = CH$_3$

In the formulae above, R$_1$ to R$_3$ are as defined for formula I.

Benzoylisocyanates of formula III can be obtained, inter alia, as follows (q.v. J. Agr. Food Chem. 21, 348 and 993; 1973):

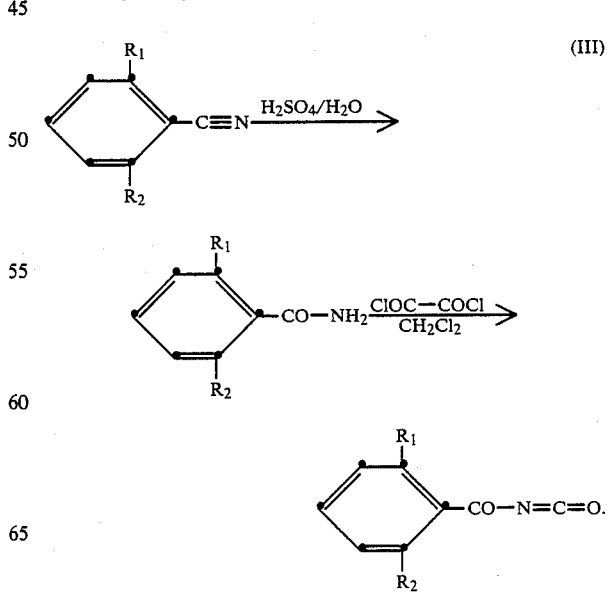

The substituted 4-pyrimidinyloxyphenylisocyanates of formula IV can be prepared e.g. by phosgenating the corresponding 4-pyrimidinyloxyanilines of formula II by methods which are commonly employed in the art (q.v. German patent specification 3 326 509). The benzamides of formula V which are further used as starting materials are known (q.v. for example Beilstein "Handbuch der organischen Chemie", Vol. 9, p. 336).

The urethanes of formula VI can be obtained in a manner known per se by reacting a benzoylisocyanate or benzoylisothiocyanate of formula III with a suitable alcohol. Urethanes of formula VI can also be prepared by reacting a benzamide of formula V, in the presence of a base, with a corresponding ester of chloroformic acid.

Insecticidal N-benzoyl-N'-pyrimidyloxyphenylureas in which the phenyl group contains a pyrimidin-5-yloxy radical are disclosed in German Offenlegungsschrift 3 311 703. Insecticidal N-benzoyl-N'-pyrimidin-2-yloxyphenylureas in which the 5-pyrimidinyl radical is substituted by halogen or trifluoromethyl, but not by an aromatic radical, are also cited in Japanese patent publication 56015-272. Compared with these prior art compounds, the compounds of formula I of this invention differ essentially in structure by virtue of the fact that their phenyl radical is substituted by a pyrimidin-2-yloxy group which itself carries a phenyl group in 5-position.

Surprisingly, it has been found that the compounds of formula I of this invention have excellent pesticidal properties with good long-term activity while being well tolerated by plants, very well tolerated by useful animals and having low toxicity to warm-blooded animals. They are especially effective for controlling representatives of the order Acarina that attack plants and animals and for controlling insects.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina of the families: Ixodidae, Argasidae, Tetranychidae and Dermanyssidae.

In addition to their action against flies, e.g. Musca domestica, and mosquito larvae, the compounds of formula I are also suitable for controlling plant-destructive feeding insects in ornamentals and crops of useful plants, especially in cotton (e.g. against Spodoptera littoralis and Heliothis virescens) and in fruit and vegetables (e.g. against Laspeyresia pomonella, Leptinotarsa decemlineata and Epilachna varivestis). The compounds of formula I have a pronounced larvicidal and ovolarvicidal action against insects, especially against larvae of noxious feeding insects. If compounds of formula I are ingested by adult insect stages with the feed, then a diminished oviposition and/or reduced hatching rate is observed in many insects, especially in Coleopterae, e.g. Anthonomus grandis.

The compounds of formula I can also be used for controlling ectoparasites such as Lucilia sericata, in domestic animals and productive livestock, e.g. by treating animals, cowsheds, barns, stables, and pastures.

The compounds of formula I are particularly effective against plant-destructive acarids (spider mites e.g. of the families Tetranychidae, Tarsonemidae, Eriophydae, Tyroglyphidae and Glycyphagidae) and also against ectoparasitic acarids (mites and ticks e.g. of the families Ixodidae, Argasidae, Sarcoptidae and Dermanissidae) that attack productive livestock. A number of the compounds of this invention have good acaricidal-ovicidal activity and leaf penetration properties. The compounds of formula I are particularly suitable for controlling the following species of mites which attack crops of fruit and vegetables: Tetranychus urticae, Tetranychus cinnabarinus, Panonychus ulmi, Broybia rubrioculus, Panonychus citri, Eriophyes piri, Eriophyes ribis, Eriophyes vitis, Tarsonemus pallidus, Phyllocoptes vitis and Phyllocoptruta oleivora.

The good pesticidal activity of the compounds of formula I of the invention corresponds to a mortality of at least 50–60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp. Ridgewood, New Jersey, 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant. Whereas commercial products are preferably formulated as concentrates, the end user will normally employ dilute formulations of substantially lower concentration, e.g. from 0.1 to 1000 ppm.

The compositions may also contain further ingredients, such as stabilisers, antifoams, viscosity regulators, binders, tackifiers as well as fertilisers or other active ingredients for obtaining special effects.

EXAMPLE 1

Preparation of starting material and intermediates (a) Preparation of 1,1,1-trifluoro-3-phenyl-4-methoxy-3-buten-2-one In an atmosphere of argon, 201 ml of trifluoroacetic anhydride are slowly added dropwise at $-10°$ to $0°$ C. to a solution of 150 g of β-methoxystyrene and 27.4 ml of pyridine in 450 ml of methylene chloride. The reaction mixture is then stirred without cooling and thereafter refluxed for 17 hours. After it has cooled, the solution is poured into 600 ml of ice-water. The organic phase is separated and washed with water, 1N sodium bicarbonate solution and then with a saturated solution of sodium chloride and dried over magnesium sulfate. The solvent is stripped off by rotary evaporation and the red liquid so obtained is distilled under a high vacuum, affording the title compound of formula

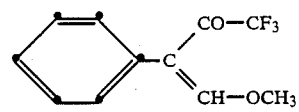

with a boiling point of $81°-84°$ C./$10^{-2}$ mm.

(b) Preparation of 2-methylthio-4-trifluoromethyl-5-phenylpyrimidine 46 g of 1,1,1-trifluoro-3-phenyl-4-methoxy-3-buten-4-one are added dropwise to a mixture of 150 ml of a 30% aqueous solution of potassium carbonate, 200 ml of ethanol and 28 g of S-methylisothiourea sulfate. The reaction mixture is then refluxed for 34 hours. After removing the ethanol by distillation, the residue is added to ice-water and extracted with ether. The solvent is distilled off and the residual red liquid is purified by column chromatography, affording the title compound of formula

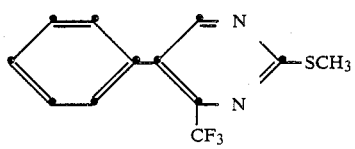

with a refractive index of $n_D^{20} = 1.5716$.

(c) Preparation of 2-methylsulfonyl-4-trifluoromethyl-5-phenylpyrimidine

With stirring, a solution of 26 g of 40% peracetic acid in 20 ml of chloroform is slowly added dropwise over 2 hours to a solution, cooled to 5° C., of 18.5 g of 2-methylthio-4-trifluoromethyl-5-phenylpyrimidine in 500 ml of chloroform, such that the temperature does not exceed 10° C. The reaction mixture is then stirred for 70 hours at room temperature until a thin-layer chromatogram no longer shows the presence of starting material. The filtered solution is then evaporated to dryness under vacuum, to give pale yellow crystals of the title compound of the formula

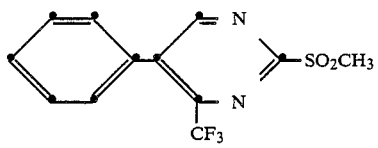

with a melting point of 110°–112° C.

(d) Preparation of 4-(4-trifluoromethyl-5-phenylpyrimidine-2-yloxy)aniline

With cooling, 2.2 g of powdered potassium hydroxide are added to a solution of 2.1 g of 4-aminophenol in 50 ml of dimethylsulfoxide and the mixture is stirred for 1 hour to form a clear solution. To the batch are then added, in portions, 6 g of 2-methylsulfonyl-4-trifluoromethyl-5-phenylpyrimidine and the mixture is stirred for 4 hours at room temperature. The mixture is then poured into ice-water and extracted with ether. The washed and dried ethereal extracts yield a product of m.p. 123°–126° C., which is the title compound of formula

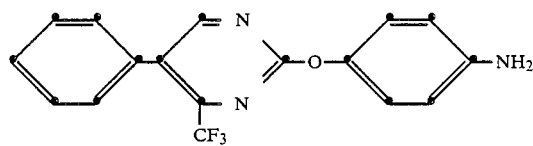

EXAMPLE 2

Preparation of N-(2,6-difluorobenzoyl)-N'-[(5-phenyl-4-trifluoromethylpyrimid-2-yloxy)phenylurea A solution of 3 g of 2,6-difluorobenzoylisocyanate in 15 ml of toluene is added dropwise to a solution (heated to 60° C. and stirred under nitrogen) of 6 g of 4-(4-trifluoromethyl-5-phenylpyrimidin-2-yloxy)aniline in 100 ml of dry toluene. After the exothermic reaction has subsided, stirring is continued for 1 hour at 80° C. The orange reaction solution is cooled and diluted with 50 ml of hexane. The precipitate is filtered with suction, washed with ether and dried, affording 5.5 g of a beige-coloured crystalline powder of m.p. 197°–199° C., which is the title compound of formula

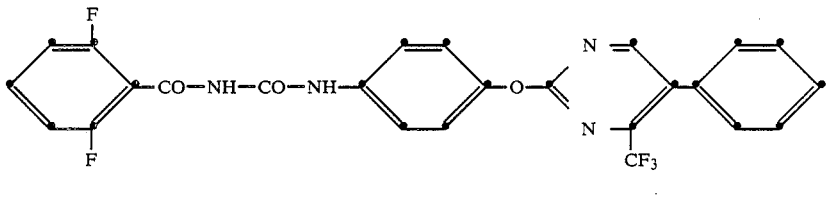

(compound 1).

The following compounds of formula I are prepared as described in the foregoing Examples:

| Compound | $X_1$ | $X_2$ | $Y_1$ | $Y_2$ | $Y_3$ | $Y_4$ | Z | $R_1$ | $R_2$ | $R_3$ | m.p.[°C.] |
|---|---|---|---|---|---|---|---|---|---|---|---|
| 2 | Cl | Cl | H | H | H | H | —CF$_3$ | H | H | H | >105° (dec.) |
| 3 | F | F | H | Cl | H | H | —CF$_3$ | H | H | H | 188–191° |
| 4 | F | F | H | Cl | Cl | H | —CF$_3$ | H | H | H | 181–4° |
| 5 | F | F | —CH$_3$ | H | H | H | —CF$_3$ | H | H | H | 183–6° |
| 6 | —OCH$_3$ | F | H | H | H | H | —CF$_3$ | H | H | H | 154–8° |
| 7 | Cl | H | H | Cl | Cl | H | —CF$_3$ | H | H | H | 234–7° |
| 8 | —SCH$_3$ | F | H | H | H | H | —CF$_3$ | H | H | H | 138–141° |
| 9 | Cl | H | H | Cl | H | H | —CF$_3$ | H | H | H | 201–4° |
| 10 | F | F | H | H | H | H | —CF$_2$Cl | H | H | H | 196–7° |
| 11 | Cl | H | H | H | H | H | —CF$_2$Cl | H | H | H | 186–7° |
| 12 | Cl | H | H | H | H | H | —CF$_3$ | H | H | H | 195–7° |
| 13 | F | F | H | H | H | H | —CH$_3$ | H | H | H | 199–200° |
| 14 | Cl | H | H | H | H | H | —CH$_3$ | H | H | H | 171–3° |
| 15 | F | F | H | —CH$_3$ | H | H | —CF$_3$ | H | H | H | 186–8° |
| 16 | F | F | H | H | H | H | —CF$_3$ | 4-Cl | H | H | 182–4° amorphous solid |
| 17 | F | F | H | Cl | H | Cl | —CF$_3$ | H | H | H | |
| 18 | F | H | H | Cl | H | Cl | —CF$_3$ | H | H | H | 195–7° |
| 19 | F | F | —CH$_3$ | H | H | —CH$_3$ | —CF$_3$ | H | H | H | 174–7° |
| 20 | Cl | Cl | —CH$_3$ | H | H | —CH$_3$ | —CF$_3$ | H | H | H | 184–8° |

-continued

| Compound | $X_1$ | $X_2$ | $Y_1$ | $Y_2$ | $Y_3$ | $Y_4$ | Z | $R_1$ | $R_2$ | $R_3$ | m.p.[°C.] |
|---|---|---|---|---|---|---|---|---|---|---|---|
| 21 | F  | F  | H    | H | H | H | —CF$_3$    | 2-F  | H | H | 175-7° |
| 22 | Cl | Cl | H    | H | H | H | —CF$_3$    | 2-F  | H | H | 215-7° |
| 23 | F  | F  | —CH$_3$ | H | H | H | —CF$_3$    | 2-F  | H | H | 161-3° |
| 24 | F  | F  | H    | H | H | H | —CF$_3$    | 2-Cl | H | H | 194-5° |
| 25 | F  | F  | —CH$_3$ | H | H | H | —CF$_3$    | 3-Cl | H | H | 190-2° |
| 26 | F  | F  | H    | H | H | H | —CF$_3$    | 3-Cl | H | H | 168-170° |
| 27 | F  | F  | —CH$_3$ | H | H | H | —CF$_3$    | 2-Cl | H | H | 197-199° |
| 28 | Cl | Cl | —CH$_3$ | H | H | H | —CF$_3$    | 2-F  | H | H | 105-6° |
| 29 | Cl | Cl | —CH$_3$ | H | H | H | —CF$_3$    | 2-Cl | H | H | 156-9° |
| 30 | F  | F  | —CH$_3$ | H | H | H | —CF$_2$Cl  | 2-Cl | H | H | 177-9° |
| 31 | F  | F  | F    | H | H | H | —CF$_3$    | H    | H | H | 192-3° |
| 32 | F  | F  | —CF$_3$ | H | H | H | —CF$_3$    | H    | H | H | 158-160° |
| 33 | F  | F  | H    | H | H | H | —CF$_2$CF$_3$ | H | H | H | 178-180° |
| 34 | Cl | Cl | H    | H | H | H | —CF$_2$CF$_3$ | H | H | H | 203-205° |

EXAMPLE 3

Formulations for active ingredients of formula I according to Example 2 or combinations thereof with other insecticides or acaricides (throughout, percentages are by weight)

| 3.1. Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affirdung wettable powders which can be diluted with water to give suspensions of the desired concentration.

| 3.2. Emulsifiable concentrate | |
|---|---|
| compound of formula I or combination | 10% |
| octylphenol polyethylene glycol ether (4–5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| 3.3. Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carrier, and grinding the mixture in a suitable mill.

| 3.4. Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 3.5. Coated granulate | |
|---|---|
| compound of formula I or combination | 3% |
| polyethylene glycol 200 | 3% |
| kaolin | 94% |

The finely ground active ingredient or combination is uniformly applied, in a mixer, to the kaolin moistened with polyethylene glycol. Non-dusty coated granulates are obtained in this manner.

| 3.6. Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

EXAMPLE 4

Action against *Musca domestica*

50 g of freshly prepared nutrient substrate for maggots are charged into each of a number of beakers. A specific amount of an acetonic solution containing 1% by weight of the respective test compound is pipetted onto the nutrient substrate present in the beakers to give an active ingredient concentration of 800 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formula I according to Example 2 exhibit good activity in this test

EXAMPLE 5

Action against *Tetranychus urticae* (OP-sensitive) and *Tetranychus cinnabarinus* (OP-tolerant)

12 hours before the test for acaricidal action, the primary leaves of *Phaseolus vulgaris* plants are infected with an infested piece of leaf from a mass culture of *Tetranychus urticae* (OP-sensitive) or *Tetranychus cinnabarinus* (OP-tolerant). (The tolerance refers to the tolerance to diazinone). The treated infested plants are sprayed to drip point with an emulsified test solution containing the respective test compound in a concentration of 400 ppm. A count of the number of living and dead imagines and larvae (all mobile stages) is made under a stereoscopic microscope after 24 hours and again after 6 days (*T. urticae*) and after 7 days (*T. cinnabarinus*). One plant is used for each test species. During the test run, the plants are kept in greenhouse compartments at 25° C. and c. 50–60% relative humidity.

In this test, compound 1 according to Example 2 effects 90–100% kill against *Tetranychus urticae* and is very effective against *Tetranychus cinnabarinus*.

EXAMPLE 6

Ovicidal action against *Tetranychus urticae* (OP-resistant)

Potted *Phaseolus vulgaris* plants in the primary leaf stage are each populated twice with 30 females of *Tetranychus urticae*. After oviposition for 24 hours, the females are removed from the plants with a suction pump (water jet pump), so that only the egg deposits on the plants remain. The egg-infested plants are then sprayed to drip point with an aqueous emulsion containing 400 ppm of the test compound and kept for 5 days at 25° C. and about 50% relative humidity. After this time a count is made to determine the percentage mortality of the eggs and of hatched out larvae.

Compounds of formula I according to Example 1 exhibit good activity in this test.

EXAMPLE 7

Miticidal leaf penetration action against *Tetranychus cinnabarinus*

Potted dwarf bean plants in the primary leaf stage infested with *Tetranychus cinnabarinus* are used for the test. The plants are populated with the mites one day before the application of the test compound.

The surface of the leaves of the plants infected with the mites are sprayed with an emulsion formulation containing 400 ppm of the test compound. After the spray coating has dried, a ribbon of viscous glue (caterpillar glue) is applied to the edge of the surface of each of a number of infested leaves so as to prevent the mites from migrating from the underside to the surface of the leaf.

The treated plants are then kept in a greenhouse at a temperature of 25°–27° C. and a relative humidity of c. 50%. Six days after application the plants are examined to ascertain whether a tranlaminar effect has occurred, i.e. penetration of the test compound from the surface to the underside of the leaf, by determining the percentage mortality of the eggs and larval as well as adult stages.

Compounds of formula I according to Example 2 exhibit good activity in this test.

EXAMPLE 8

Action against *Panonychus ulmi* (OP and carbamate resistant)

Potted apple seedlings with about 20 to 30 leaves are each populated with 60 adult females of *Panonychus ulmi*. The infested plants are sprayed after 7 days to drip point with an aqueous emulsion containing 400 ppm of the test compound. The treated plants are then stood in a greenhouse for a further 14 days at 25° C. and about 50% relative humidity.

After this time, evaluation is made by taking 20 leaves from each plant, removing the mite population from these leaves by means of a brushing device and counting the number of eggs, postembryonic stages and adults under a stereoscopic microscope. An assessment is made of the percentage reduction of the mite population as compared with untreated controls.

Compounds of formula I according to Example 2 exhibit good activity in this test.

EXAMPLE 9

Action against parasitic mites in animals

Batches consisting of about 50 mites in different stages (larvae, nymphs and imagines) are taken from hens infested with *Dermanyssae gallinae*. The batches are each treated with an aqueous emulsion, suspension or solution containing 800 ppm of the test compound by pouring the liquid formulation of the test compound on to the mites present in a test tube. The liquid formulation is then absorbed by a cotton wool plug. The treated mites remain in the test tube for 72 hours, after which time the percentage mortality of the treated mites is determined in comparison with untreated controls.

Compounds of formula I according to Example 2 exhibit good activity in this test.

EXAMPLE 10

Action against ticks: killing action in various development stages

About 50 larvae, about 25 nymphs or about 10 imagines of each of the tick species *Rhipicephalus bursa*, *Amblyomma hebraeum* and *Boophilus microplus* are used as test organisms. The test organisms are immersed for a short time in aqueous emulsions containing the respective test compound in a concentration of 400 ppm. The emulsions, which are contained in test tubes, are then absorbed by cotton wool, and the wetted test organisms are left in the test tubes which have thus been contaminated. Evaluation of the percentage mortality is made 3 days later in the case of the larvae and 14 days later in the case of the nymphs and imagines.

Compounds of formula I according to Example 2 are very effective in this test.

EXAMPLE 11

Action against ticks: inhibition of oviposition

Adult females of the cattle tick *Boophilus microplus* which are fully replete with blood are used as test organisms. 10 ticks of an OP-sensitive strain (e.g. Biarra strain) and 10 ticks of a normally sensitive strain (e.g. Yeerongpilly strain) are treated. The ticks are affixed to plates to which double-sided adhesive tape has been applied and are then either wetted with aqueous emulsions or solutions containing 800 ppm of the test compound or are brought into contact with cotton wool which has been impregnated with these liquids. The ticks are subsequently kept in a climatic chamber under constant conditions. Evaluation is made after 3 weeks. The percentage inhibition of the deposit of fertile eggs is determined in comparison with untreated controls.

Compounds of formula I according to Example 2 exhibit good activity in this test.

EXAMPLE 12

Action against *Aëdes aegypti*

A concentration of 800 ppm is obtained by pipetting a specific amount of a 0.1% solution of the test compound in acetone onto the surface of 150 ml of water in a beaker. After the acetone has evaporated, 30 to 40 two-day-old larvae of *Aëdes aegypti* are put into the beaker containing the test compound. Mortality counts are made after 1, 2 and 5 days.

Compounds of formula I according to Example 2 exhibit good activity against *Aëdes aegypti* in this test.

EXAMPLE 13

Insecticidal action against feeding insects

Cotton plants about 25 cm high, in pots, are sprayed with aqueous emulsions which contain the respective test compound in a concentration of 400 ppm. After the spray coating has dried, the cotton plants are populated with *Spodoptera littoralis* and *Heliothis virescens* larvae in the L₃-stage. The test is carried out at 24° C. and 60% relative humidity. The percentage mortality of the test insects is determined after 120 hours.

Compounds of formula I according to Example 2 are very effective in this test.

EXAMPLE 14

Action against *Laspeyresia pomonella* (eggs)

Egg deposits of *Laspeyresia pomonella* not more than 24 hours old are immersed on filter paper for 1 minute in an aqueous acetonic solution containing 800 ppm of the test compound.

After the solution has dried, the filter paper and the eggs are placed in petri dishes and kept at a temperature of 28° C. The percentage of larvae hatched from the treated eggs is evaluated after 6 days and the percentage mortality determined.

Compounds of formula I according to Example 2 are very effective in this test.

EXAMPLE 15

Influence on the reproduction of *Anthonomus grandis*

*Anthonomus grandis* adults which are not more than 24 hours old after hatching are transferred in groups of 25 to barred cages. The cages are then immersed for 5 to 10 seconds in an acetonic solution containing 400 ppm by weight of the test compound. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine the percentage mortality of the eggs, i.e. how many larvae have developed from the eggs.

The duration of the reproduction inhibiting effect of the test compounds is determined by monitoring the egg deposits of the beetles further, i.e. over a period of about 4 weeks. Evaluation is made by assessing the reduction in the number of deposited eggs and larvae hatched from them in comparison with untreated controls.

Compounds of formula I according to Example 2 exhibit good activity in this test.

What is claimed is:

1. A compound of formula I

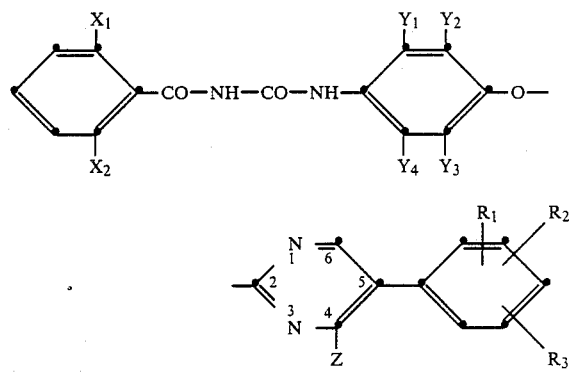

wherein
- $X_1$ is hydrogen, halogen, $C_1$–$C_3$alkoxy or $C_1$–$C_3$alkylthio,
- $X_2$ is halogen, methyl, $C_1$–$C_3$alkoxy or $C_1$–$C_3$alkylthio,
- $Y_1$, $Y_2$, $Y_3$ and $Y_4$ are each independently hydrogen, halogen, methyl, trifluoromethyl or methoxy,
- Z is methyl, halomethyl containing 1 to 3 halogen atoms or pentafluoroethyl; and
- $R_1$, $R_2$ and $R_3$ are each independently hydrogen, halogen, $C_1$–$C_3$alkyl, trifluoromethyl or $C_1$–$C_3$alkoxy.

2. A compound of formula I according to claim 1, wherein
- $X_1$ is hydrogen, halogen, $C_1$–$C_3$alkoxy or $C_1$–$C_3$alkylthio,
- $X_2$ is halogen, methyl, $C_1$–$C_3$alkoxy or $C_1$–$C_3$alkylthio,
- $Y_1$, $Y_2$, $Y_3$ and $Y_4$ are each independently hydrogen, halogen, methyl, trifluoromethyl or methoxy,
- Z is methyl or halomethyl containing 1 to 3 halogen atoms; and
- $R_1$, $R_2$ and $R_3$ are each independently hydrogen, halogen, $C_1$–$C_3$alkyl, trifluoromethyl or $C_1$–$C_3$alkoxy.

3. A compound of formula I according to claim 1, wherein
- $X_1$ is hydrogen, halogen or methoxy,
- $X_2$ is halogen or methoxy,
- $Y_1$ and $Y_4$ are hydrogen,
- $Y_2$ and $Y_3$ are each independently of the other hydrogen, fluorine, chlorine, methyl or trifluoromethyl, Z is methyl, dichloromethyl, trichloromethyl, monofluoromethyl, difluoromethyl, trifluoromethyl, difluorochloromethyl or pentafluoroethyl; and $R_1$, $R_2$ and $R_3$ are each independently hydrogen, fluorine, chlorine, bromine, methyl, ethyl, isopropyl, trifluoromethyl, methoxy or ethoxy.

4. A compound of formula I according to claim 1, wherein $X_1$ is fluorine, chlorine or methoxy, and $X_2$ is fluorine or chlorine.

5. A compound of formula I according to claim 1, wherein $Y_1$ is methyl and $Y_2$, $Y_3$ and $Y_4$ are hydrogen.

6. A compound of formula I according to claim 1, wherein $Y_1$ and $Y_4$ are hydrogen, and $Y_2$ and $Y_3$ are hydrogen, fluorine or chlorine.

7. A compound of formula I according to claim 1, wherein Z is trifluoromethyl, difluorochloromethyl or pentafluoroethyl.

8. A compound of formula I according to claim 1, wherein $R_1$ is hydrogen, $R_2$ is hydrogen, 2-fluoro or 2-chloro, and $R_3$ is hydrogen, 4-fluoro or 4-chloro.

9. A compound according to claim 1, wherein $X_1$ and $X_2$ are fluorine.

10. A compound of formula I according to claim 1, wherein $R_1$, $R_2$ and $R_3$ are hydrogen.

11. A compound according to claim 7 of formula

12. A compound according to claim 7 of formula

13. A compound according to claim 7 of formula

14. A compound according to claim 7 of formula

15. A pesticidal composition which comprises as active ingredient, a pesticidally effective amount of a compound according to claim 1, together with a suitable carrier or other adjuvant.

16. A method of controlling pests selected from insects and representatives of the order Acarina, which method comprises contacting or treating said pests, their various development stages or the locus thereof with a pesticidally effective amount of a compound of formula I according to claim 1.

17. A method according to claim 16 for controlling plant-destructive acarids.

18. A compound of formula II, wherein $Y_1$, $Y_2$, $Y_3$ and $Y_4$ are each independently hydrogen, halogen, methyl, trifluoromethyl or methoxy, Z is methyl, halomethyl containing 1 to 3 halogen atoms or pentafluoroethyl; and $R_1$, $R_2$ and $R_3$ are each independently hydrogen, halogen, $C_1$-$C_3$alkyl, trifluoromethyl or $C_1$-$C_3$alkoxy.

19. A compound of formula IV,

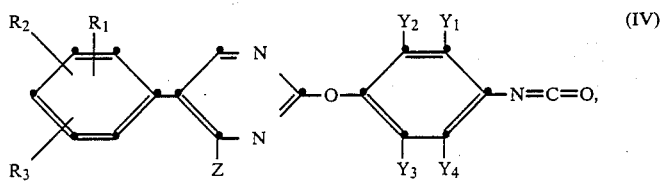

wherein
 $Y_1$, $Y_2$, $Y_3$ and $Y_4$ are each independently hydrogen, halogen, methyl, trifluoromethyl or methoxy,
 Z is methyl, halomethyl containing 1 to 3 halogen atoms or pentafluoroethyl; and
 $R_1$, $R_2$ and $R_3$ are each independently hydrogen, halogen, $C_1$–$C_3$alkyl, trifluoromethyl or $C_1$–$C_3$alkoxy.

20. A method of controlling pests selected from insects and representatives of the order Acarina, which method comprises contacting or treating said pests, their various development stages or the locus thereof with a pesticidally effective amount of a composition according to claim 15.

* * * * *